United States Patent [19]

Nichols et al.

[11] 4,313,339

[45] Feb. 2, 1982

[54] RHEOMETER AND RHEOLOGICAL MEASURING METHOD

[75] Inventors: Walter A. Nichols, Richmond; George L. Mathe, Bon Air, both of Va.

[73] Assignee: Philip Morris Incorporated, New York, N.Y.

[21] Appl. No.: 131,745

[22] Filed: Mar. 19, 1980

[51] Int. Cl.³ ............................................ G01N 11/04
[52] U.S. Cl. ...................................................... 73/56
[58] Field of Search ...................... 73/56, 55; 222/243; 417/430

[56] References Cited

U.S. PATENT DOCUMENTS 3,360,986  1/1968  Rothschild ............................... 73/56
3,443,520  5/1969  Nejame ............................ 417/430 X

FOREIGN PATENT DOCUMENTS 148267  11/1966  U.S.S.R. ................................... 73/56

Primary Examiner—Jerry W. Myracle
Attorney, Agent, or Firm—Robert M. Shaw

[57] ABSTRACT

A rheometer of the extrusion plastometer type is provided with means for forcibly mechanically mixing the material to be tested within the chamber of the rheometer. The rheometer preferably includes a pair of telescopically arranged pistons which can be selectively coupled and uncoupled from one another so that one of them can serve as a mixing device. The pistons are coupled for unitary movement when discharging the material being tested.

22 Claims, 3 Drawing Figures

RHEOMETER AND RHEOLOGICAL MEASURING METHOD

BACKGROUND OF THE INVENTION

The present invention relates to the art of rheological measurements and more particularly relates to an improved rheometer of the extrusion plastometer type and to an improved rheological measuring method.

Various types of rheometers are known. Such devices are utilized in the testing of flowable materials to determine their rheological characteristics, such as viscosity. Representative of such devices are those disclosed in U.S. Pat. Nos. 1,506,617; 1,664,839; 1,919,921; 2,028,187; 2,834,200; 3,036,214; 3,209,581; 3,283,565; 3,559,464; 3,595,305; 3,681,980; 3,766,773; 3,805,598; 3,908,442; 3,930,403; 3,933,032; 3,935,729. Another such representative device has been described by D. E. Elliott and P. J. Chiesa in an article entitled "A New Foam Rheometer for Studying Fire Fighting Foams," *Fire Technology*, Vol. 12, No. 1, pp. 66-69 (1976).

One important form of rheometer which has gained wide acceptance, especially in the plastics industry, is the so-called "extrusion plastometer". The extrusion plastometer incorporates a chamber having a discharge orifice and means for controllably forcing material from the chamber through the discharge orifice. Thus, a charge of the material to be tested is loaded into the chamber and then forced out through the orifice. While the material is being forced out, the various parameters of the system, such as the amount of pressure applied to the material and the amount of material discharged per unit time are controlled or monitored. From these parameters, and from the known dimensions of the discharge orifice, the rheological properties of the material may be determined. Various forms of extrusion plastometer have been described in ASTM test method D1238 (American Society for Testing and Materials, Philadelphia, Pa.) and in the following U.S. Pat. Nos.: 3,203,225; 3,242,720; and 3,360,986.

However, prior to the present invention, no extrusion plastometer which is truly satisfactory for measuring the rheological properties of a multi-component mixture has been available. Such mixtures are frequently encountered in industrial practice. For example, one commercially important mixture includes a polyolefin polymer, a nucleating agent and a foaming agent such as a monomeric halogenated hydrocarbon. Because the properties of such a mixture change with time from the moment that the foaming agent is mixed with the other components, it is desirable to measure the rheological properties of the mixture immediately after mixing. However, with the extrusion plastometers the prior art, it has generally been necessary to first mix the various components outside of the chamber and then load the mixture into the chamber. As will be readily appreciated, such a procedure may entail some delay between mixing and measurement of rheological properties, which may cause the properties to change and may result in an inaccurate determination.

SUMMARY OF THE INVENTION

It is an object of the present invention to provide an improved rheometer which retains all of the desirable characteristics of the extrusion plastometer, and which can be utilized in a manner analagous to the use of a conventional extrusion plastometer, but which substantially obviates the aforementioned difficulty.

It is a further object of the present invention to provide an improved method of measuring the rheological properties of a material which method is substantially free of the aforementioned difficulty.

The rheometer apparatus of the present invention includes a jacket which defines a bore and a discharge end structure which substantially occludes a discharge end of the bore. The discharge end structure has an orifice which extends through it and which communicates with the bore. Discharge control means are provided for selectively occluding the orifice. Loading means are provided for introducing the material to be tested into the bore. The apparatus also includes pressure means for controllably pressurizing any material contained in the bore, and means for forcibly mechanically mixing material contained in the bore are provided.

Thus, the material to be tested can be loaded into the bore and temporarily retained in the bore by setting the discharge control means to occlude the orifice. While the material to be tested is so retained, it can be mixed within the chamber. After the material has been mixed, the discharge control means may be set so that the orifice is open and the pressure means may be actuated to controllably force the mixed material through the orifice. While the material is being forced through the orifice, the pressure applied to the material and the amount of material discharged per unit time may be controlled or monitored in the conventional manner so that the rheological properties of the material may be determined.

Because the material to be tested can be mixed within the bore of the apparatus of the present invention, such apparatus possesses important advantages. If the material to be tested is made up of multiple components, the components need not be mixed with one another before they are introduced into the bore. Therefore, the problems of reaction and time dependent decay of such a mixture are substantially reduced.

Also, the mixing of the material within the bore promotes rapid thermal equilibration of the material. Thus the material need not be held in the bore of the apparatus for a prolonged period to assure thermal equilibration.

Preferably, the means for mixing the material within the bore includes a first piston which is slidably received in the bore. The first piston defines a passageway which extends between its faces. The pressure means preferably includes a second piston which is slidably received in the bore. The first piston is disposed between the second piston and the discharge end of the bore. Apparatus of the present invention which includes such pistons also has piston control means for controllably sliding each of the pistons within the bore. Thus, material retained in the bore can be mixed by reciprocating the first piston to force the material through the passageway. The material can be pressurized to discharge it through the orifice by advancing the piston towards the discharge end of the bore.

Preferably, the piston control means includes a first rod fixed at one end to the first piston and extending through a bore in the second piston. The piston control means also preferably includes a tubular second rod fixed at one end to the second piston and surrounding the first rod. The piston control means is preferably arranged so that the first and second pistons may be selectively linked for motion in unison with one another. Preferably, the piston control means is arranged so that while the pistons are so linked, the first piston abuts the second piston. Thus, immediately before the second piston is advanced to discharge the material, the first piston is locked into abutting relation with it so that the pistons advance as a unit.

In the measuring method of the present invention, the material to be tested is loaded into a chamber having a discharge orifice. The discharge orifice of the chamber is occluded to retain the material within the chamber. While the material to be tested is so retained it is forcibly mechanically mixed. After the material has been mixed it is forced out through the discharge orifice in a controlled manner and the discharge is monitored. Thus, the rheological properties of the mixed material may be determined. The method of the present invention possesses advantages analagous to the advantages of the apparatus described above.

BRIEF DESCRIPTION OF THE DRAWINGS

A fuller understanding of the nature and objects of the present invention will be had from the following detailed description taken in conjunction with the accompanying drawings in which.

Throughout the following description, like reference numerals are used to denote like parts in the drawings.

DESCRIPTION OF THE PREFERRED EMBODIMENTS

Figure 1:
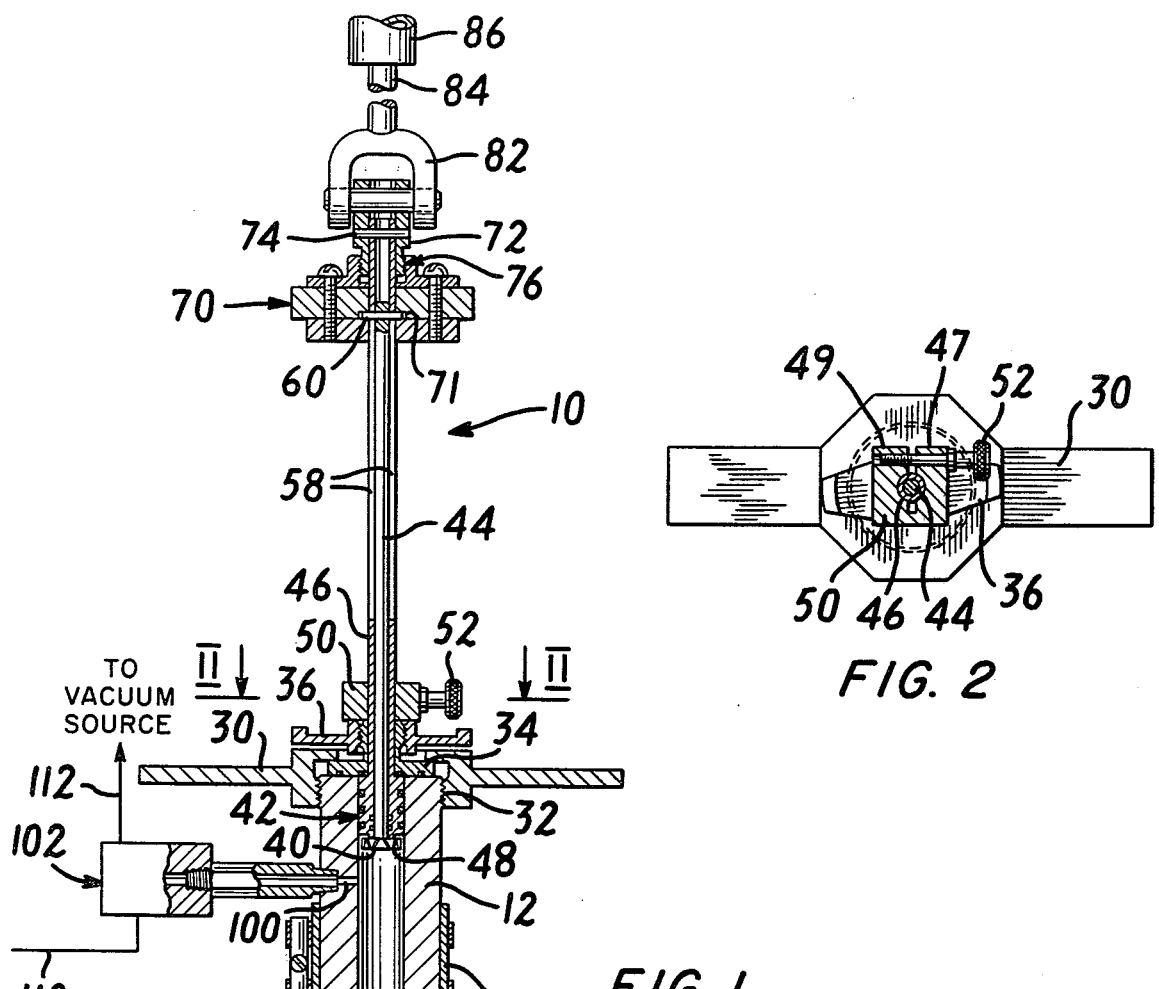
FIG. 1 is a vertical elevational view in section of a rheometer device according to the preferred embodiment of the present invention, the two pistons and associated rods which are received in the bore being shown in their fully upper extended position.
Figure 3:
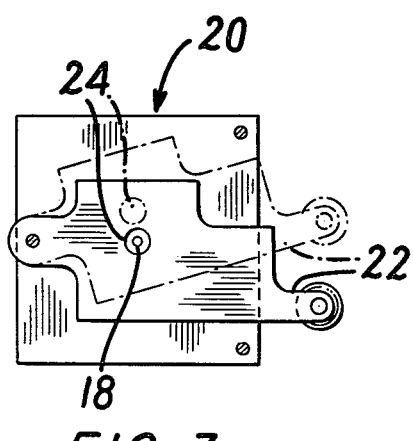

With reference to FIG. 1 of the drawings, a rheometer device 10 of the present invention includes an elongated preferably uprightly disposed jacket 12 having a thorough bore 14 therein. The lower or discharge end of the jacket 12 is capped with a disc 16 which in turn has an orifice 18 formed therein and extending therethrough. A discharge control assembly including a block 20 is threaded onto the lower end of the jacket and carries therein a pivoted plate 22. The upper surface of the plate closely overlies the lower face of the disc. The plate is movable between two positions as depicted in solid and broken lines in FIG. 3. In a first one of the positions, depicted in broken lines in FIG. 3, the plate 22 closes off the orifice 18 in disc 16 so that any contents present within the bore remain therein. On the other hand, when it is desired to discharge the contents from the bore 14 the plate 22 is moved to the position shown in solid lines in FIG. 3 and an aperture 24 therein comes into register with the orifice 18 to thereby permit outflow of material from the jacket bore. The block 20 can be unthreaded from the jacket so that the disc 16 may be removed from the jacket and replaced with another disc having a different orifice.

At the upper end of the jacket 12, there is provided a support plate 30 from which the jacket can be suspended with the threaded connection shown generally at 32. A capping plate 34 is fitted over the upper end of the jacket and is releasably secured to the jacket by the plate 30. A spinner unit 36 is threadedly engaged with the capping plate 34.

Received within the bore 14 are a pair of pistons 40 and 42, each of which has a respective piston rod 44 and 46 fixedly connected thereto. The piston rods, which are shown in their fully upwardly retracted position in FIG. 1, are arranged in a telescopic configuration such that the first rod 44 associated with the first piston 40 extends in slidable sealing engagement through a bore in the second piston 42 and is slidably received inside of the tubular second rod 46 associated with second piston 42. The first piston 40 is provided with a plurality of passages 48 extending through it from face to face thereof. As will appear later in the description, the first piston 40 is intended to be employed as a mixing device for mixing materials present within the bore.

Figure 2:
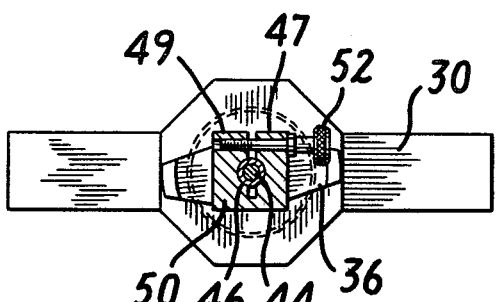
FIGS. 2 and 3 are sectional views taken along the section lines 2—2 and 3—3 respectively in FIG. 1.

Encircling the outer piston rod 46 and resting on the spinner unit 36 is a stop device including a split block 50 which is provided with a locking screw 52. The screw 52 can be used to urge the respective branches 47 and 49 (FIG. 2) of the split block into tight clamping relationship with the second rod 46. By thus employing this stop device, sliding travel of rod 46 can be prevented whenever it is desired to merely slide the first piston 40 and its associated rod 44 in the mixing operation.

The second rod 46 is, for an appreciable portion of its length, provided with slots 58 disposed at 180° orientation with each other. A connector 60 is fixed to the upper end of the first piston rod 44 and extends through the slots 58 in the second piston rod. A disc-like first piston control block 70 encircles the second rod, and is provided with an annular groove 71 which is substantially concentric with the piston rods. The connector 60 is received in the groove 71. Thus, the first piston rod 44 is linked to the first piston control block 70, but that block may be rotated about the rods.

A second piston control block 72 is fixed to the upper end of the second piston rod 46 by a pin 74. Mating threads, indicated generally at 76, are provided on the lower end of the second piston control block 72 and on the upper end of the first piston control block 70. In the position illustrated in FIG. 1, the blocks are threadedly engaged with one another, so that the piston rods and pistons are coupled for movement in unison with one another. However, by rotating the first block 70, the threads may be unscrewed and the blocks may be disengaged from one another. When the blocks are disengaged, the first piston control block 70 can be manually reciprocated along the second piston rod 46. This will cause the first piston 40 to reciprocate independently of the second piston 42. During such independent reciprocation, the connector 60 travels within the slots 58 in the second piston rod 46.

The second piston control block 72 is connected to a clevis 82 carried on the piston rod 84 of a cylinder unit 86 which is used for actuating movement of the second piston 42.

Mounted on one side of the jacket 12 and communicating with the bore 14 by means of passage 100 is a three-way valve unit shown schematically at 102. The valve unit can be selectively operated to establish communication between the bore 14 and a material component source by means of line 110, or to establish communication between the bore and a vacuum source by means of line 112. The valve unit can be shut to prevent communication between the bore and the sources.

Encircling the jacket are a pair of electrical band heaters 116 which function independently of each other and which are employed for heating the jacket so as to thereby heat any materials present within the bore.

Appropriate thermostatic devices (not shown) are provided to control the power supply to the band heaters.

The apparatus described above may be utilized in the following manner. First, the capping plate 34 and the pistons are removed from the jacket and a first component of the material to be tested, such as a polymer with a nucleating agent, is poured into the bore. The capping plate and pistons are then replaced. With the two pistons 40, 42 in their upper retracted position as depicted in FIG. 1, and with the discharge control plate 22 set to occlude the orifice 18, the three-way valve 102 is suitably oriented to connect the interior of the jacket with the vacuum source to remove from the bore any gases present therein. The polymer and nucleating agent are heated in the bore by the band heaters 116. By actuating the three-way valve 102, another component of the material to be tested, such as a foaming agent, is injected into the bore from the line 110.

The stop device 50 is set to hold piston rod 46 in fixed position so that it cannot be moved. The first piston control block 70 is rotated to disengage it from the second piston control block 72. When the disengagement is complete, the first piston control block is manually reciprocated, which causes the first rod 44 and hence the first piston 40 to reciprocate. As the first piston 40 moves within the bore, the material present within the bore is forced through the passageways 48 in the first piston and is thus forcibly mixed. This action is continued to whatever extent is necessary to ensure adequate and complete mixing of the material present within the bore.

After mixing, the first piston control block 70 is engaged with the second piston control block 72 so that the first piston 40 abuts the second piston 42 and is linked therewith for movement in unison. The discharge control plate 22 is moved to align the aperture 24 in the plate with the orifice 18 in the disc 16. The clamping screw 52 is actuated to release the second piston rod 46 from engagement with the split block 50.

The cylinder unit 86 is then actuated to force the second piston 42 downwardly in a controlled manner to pressurize the material in the bore and expel it through the orifice. The first piston 40 merely travels with the second piston, and does not perform any function during the expulsion step. Of course, the valve 102 is shut during the expulsion step.

Thus, during the expulsion step, the apparatus is operated in a manner similar to the operation of a conventional extrusion plastometer. The pistons of the apparatus described above can be moved downwardly at a fixed speed, and the force required to produce such motion can be monitored to gauge the viscosity of the material being tested. Alternatively, a known load can be applied to the piston to produce a known pressure on the material within the chamber, and the amount of material forced through the orifice per unit time can be monitored to determine the viscosity of the material.

Numerous variations and combinations of the features and steps described above may be utilized without departing from the spirit of the present invention. Merely by way of example, the first piston can be provided with slots about its periphery which extend from one face to the other face of the piston so that the slot surfaces of the first piston and the bore wall surface of the jacket cooperatively define passageways. Alternatively, the first piston can be made slightly smaller in diameter than the bore, so that the first piston and the wall of the bore will cooperatively define a single, annular passageway extending between the faces of the first piston. As the first piston is reciprocated the material within the bore will be forced through the annular passageway and thus will be forcibly mixed. The apparatus and method of operation described above could be modified so that the first piston was left at the bottom of the bore as material was expelled from the bore. In this arrangement, the material would flow first through the passageways defined by the first piston and then through the orifice. The second piston used in the preferred embodiment described above could be replaced by means for controllably introducing an inert fluid under pressure at the top of the bore to pressurize the material within the bore and force it out through the orifice.

Thus, the foregoing description of preferred and alternate embodiments should be taken as merely illustrative of the present invention as defined in the appended claims.

What is claimed is:

1. Rheometer apparatus useful in internally mixing discrete components to form a multi-component material and in testing the rheological properties of multi-component materials, said apparatus comprising:
   (a) a jacket defining a bore;
   (b) a discharge end structure for occluding said bore at a discharge end thereof, said structure having an orifice which extends therethrough and which communicates with said bore;
   (c) discharge control means for selectively occluding said orifice;
   (d) loading means for introducing the material to be tested into said bore;
   (e) means within the bore for forcibly mechanically mixing discrete components contained therein, to form a multi-component material; and
   (f) pressure means for controllably pressurizing material contained in the bore to force it out through said orifice.

2. Apparatus as claimed in claim 1 wherein said means for mixing includes a first piston slidably received in said bore, said first piston defining a passageway extending between its faces, said pressure means includes a second piston slidably received in said bore, said first piston being disposed between said second piston and the discharge end of said bore, said apparatus further comprising piston control means for controllably sliding each of said pistons within said bore, whereby material retained in the bore may be mixed by reciprocating said first piston to force the material through said passageway and the mixed material may be pressurized by advancing said second piston.

3. Apparatus as claimed in claim 2 wherein said piston control means includes stop means for selectively holding said second piston in fixed relation to said jacket.

4. Apparatus as claimed in claim 3 wherein said piston control means includes means for selectively linking said first piston to said second piston for movement in unison therewith.

5. Apparatus as claimed in claim 4 wherein said second piston has a bore extending through it, said piston control means includes a first rod fixed at one end to said first piston and a second, tubular rod fixed at one end to said second piston, said first rod is slidably received in the bore of said second piston, and said first rod extends within said second rod.

6. Apparatus as claimed in claim 5 wherein said second rod is slotted over a substantial portion of its length, said piston control means includes a connector fixed to said first rod and extending through the slot in said second rod, and said piston control means also includes a first piston control block slidably mounted to said second rod and engaging said connector for sliding motion therewith.

7. Apparatus as claimed in claim 6 wherein said piston control means includes a second piston control block fixed to said second rod, and said piston control blocks have mating threads, whereby said pistons can be selectively linked for movement in unison by threadedly engaging said piston control blocks with one another.

8. Apparatus as claimed in claim 7 wherein, when said blocks are threadedly engaged with one another, said first piston abuts said second piston.

9. Apparatus as claimed in claim 5 wherein said stop means comprises a split block encircling said second rod, and means for selectively urging said split block into firm binding contact with said second rod.

10. Apparatus as claimed in claim 1, wherein said discharge end structure includes a disc releasably fixed to said jacket and covering the discharge end of said bore, said orifice extends through said disc, said discharge control means includes a plate having an aperture therein fixed to said jacket in close overlying engagement with a face of said disc, and said plate is movable from a first position in which it occludes said orifice to a second position in which said aperture registers with said orifice.

11. Apparatus as claimed in claim 1 wherein said loading means includes means for sequentially introducing discrete components of the material to be tested into said bore.

12. Apparatus as claimed in claim 1, further comprising means for selectively establishing communication between said bore and a vacuum source, whereby gases may be evacuated from said bore.

13. A method of measuring the rheological properties of a material comprising the steps of:
(a) loading the material to be tested into a chamber having a discharge orifice;
(b) occluding the discharge orifice to retain the material within the chamber and mixing the material while it is so retained; and
(c) forcing the mixed material out of the chamber through the discharge orifice in a controlled manner and monitoring the discharge to determine the rheological properties.

14. A method as claimed in claim 13 wherein the material is mixed by reciprocating a first piston within the chamber to force the material through a passageway extending between the faces of the piston.

15. A method as claimed in claim 14 wherein the material is forced out of the chamber by controllably advancing a second piston while maintaining the first piston in fixed relation to the second piston.

16. A method as claimed in claim 15 wherein the first piston is maintained in abutting relation with the second piston while the second piston is advanced.

17. A method as claimed in claim 13 wherein the material is loaded into the chamber as two discrete components.

18. A method as claimed in claim 13 futher comprising the step of evacuating gases from the chamber.

19. Rheometer apparatus comprising:
(a) a jacket defining a bore;
(b) a discharge end structure for occluding said bore at a discharge end thereof, said structure having an orifice which extends therethrough and which communicates with said bore;
(c) discharge control means for selectively occluding said orifice;
(d) loading means for introducing the material to be tested into said bore;
(e) means for forcibly mechanically mixing material contained in the bore, said means for mixing including a first piston slidably received in said bore, said first piston defining a passageway extending between its faces;
(f) pressure means for controllably pressurizing material contained in the bore to force it out through said orifice, said pressure means including a second piston slidably received in said bore, said first piston being disposed between said second piston and the discharge end of said bore; and
(g) piston control means for controllably sliding each of said pistons within said bore, whereby material retained in the bore may be mixed by reciprocating said first piston to force the material through said passageway and the mixed material may be pressurized by advancing said second piston.

20. Rheometer apparatus comprising:
(a) a jacket defining a bore;
(b) a discharge end structure for occluding said bore at a discharge end thereof, said structure having an orifice which extends therethrough and which communicates with said bore, and including a disc releasably fixed to said jacket and covering the discharge end of said bore, said orifice extending through said disc;
(c) discharge control means for selectively occluding said orifice, said discharge control means including a plate having an aperture therein fixed to said jacket in close overlying engagement with a face of said disc, said plate being movable from a first position in which it occludes said orifice to a second position in which said aperture registers with said orifice;
(d) loading means for introducing the material to be tested into said bore;
(e) pressure means for controllably pressurizing material contained in the bore to force it out through said orifice; and
(f) means for forcibly mechanically mixing material contained in the bore.

21. Rheometer apparatus comprising:
(a) a jacket defining a bore;
(b) a discharge end structure for occluding said bore at a discharge end thereof, said structure having an orifice which extends therethrough and which communicates with said bore;
(c) discharge control means for selectively occluding said orifice;
(d) loading means for introducing the material to be tested into said bore, said loading means including means for sequentially introducing discrete components of the material to be tested into said bore;
(e) pressure means for controllably pressurizing material contained in the bore to force it out through said orifice; and
(f) means for forcibly mechanically mixing material contained in the bore.

22. Rheometer apparatus comprising:
(a) a jacket defining a bore;
(b) a discharge end structure for occluding said bore at a discharge end thereof, said structure having an orifice which extends therethrough and which communicates with said bore;

(c) discharge control means for selectively occluding said orifice;

(d) loading means for introducing the material to be tested into said bore;

(e) pressure means for controllably pressurizing material contained in the bore to force it out through said orifice;

(f) means for forcibly mechanically mixing material contained in the bore; and (g) means for selectively establishing communication between said bore and a vacuum source, whereby gases may be evacuated from said bore.

* * * * *